(12) United States Patent
Coelingh Bennink

(10) Patent No.: US 9,295,720 B2
(45) Date of Patent: Mar. 29, 2016

(54) IMMUNOTHERAPEUTIC METHOD FOR TREATING PROSTATE CANCER

(75) Inventor: Herman Jan Tijmen Coelingh Bennink, Zeist (NL)

(73) Assignee: PANTARHEI BIOSCIENCE B.V., Zeist (NL)

( * ) Notice: Subject to any disclaimer, the term of this patent is extended or adjusted under 35 U.S.C. 154(b) by 283 days.

(21) Appl. No.: 13/819,622

(22) PCT Filed: Aug. 29, 2011

(86) PCT No.: PCT/NL2011/050586
§ 371 (c)(1),
(2), (4) Date: May 13, 2013

(87) PCT Pub. No.: WO2012/026820
PCT Pub. Date: Mar. 1, 2012

(65) Prior Publication Data
US 2013/0224233 A1    Aug. 29, 2013

(30) Foreign Application Priority Data
Aug. 27, 2010   (EP) .................................... 10174349

(51) Int. Cl.
*A61K 38/00* (2006.01)
*A61K 39/00* (2006.01)
*A61K 38/17* (2006.01)

(52) U.S. Cl.
CPC .............. *A61K 39/0011* (2013.01); *A61K 38/17* (2013.01); *A61K 38/00* (2013.01); *A61K 38/1764* (2013.01); *A61K 39/00* (2013.01)

(58) Field of Classification Search
CPC ... A61K 38/00; A61K 38/1764; A61K 39/00; A61K 39/0011

USPC .............. 424/277.1; 530/300, 350; 435/320.1; 514/44 R
See application file for complete search history.

(56) References Cited

U.S. PATENT DOCUMENTS

| 5,672,488 A * | 9/1997 | Dean ............................ 435/69.3 |
| 6,455,041 B1 * | 9/2002 | Dunbar ........................ 424/139.1 |
| 7,569,225 B2 * | 8/2009 | Jackson et al. ...... A61K 39/0006 424/184.1 |
| 8,367,067 B2 * | 2/2013 | Jackson ............. A61K 39/0006 424/184.1 |

FOREIGN PATENT DOCUMENTS

| WO | 0212330 A2 | 8/2001 |
| WO | 2007058536 A1 | 5/2007 |

OTHER PUBLICATIONS

Ho et al. (Blood. Apr. 15, 1993; 81 (8): 2093-101).*
Paterson et al. (Mol. Hum. Reprod. Apr. 1999; 5 (4): 342-52).*

* cited by examiner

*Primary Examiner* — Stephen Rawlings
(74) *Attorney, Agent, or Firm* — Browdy and Neimark, PLLC

(57) ABSTRACT

The invention relates to treatment of prostate cancer and metastases thereof. More specifically, the invention relates to immunogenic polypeptides comprising at least a portion of a prostatic tumor cell-associated protein or immunologically active variants thereof and to nucleic acids encoding such polypeptides and to the use thereof in immunotherapeutic methods of treatment of prostate cancer. Said immunogenic polypeptides are provided by the zona pellucida (ZP) (glyco) proteins. ZP (glyco)proteins and fragments thereof that can induce a $CD8^+$ and/or $CD4^+$ T cell response as well as nucleic acid sequences encoding them can suitably be used in the present immunotherapeutic strategies.

22 Claims, 6 Drawing Sheets

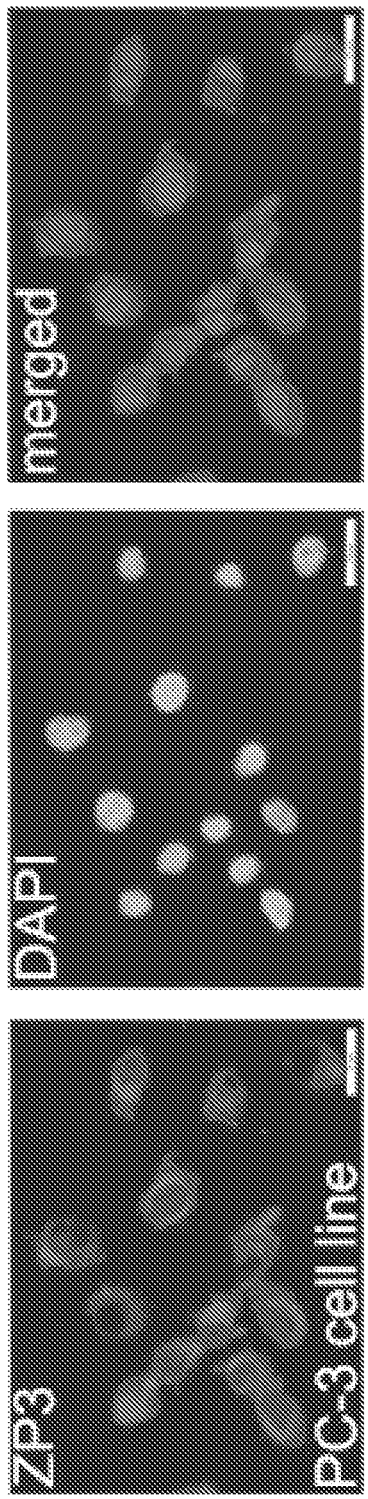

IMMUNOTHERAPEUTIC METHOD FOR TREATING PROSTATE CANCER

FIELD OF THE INVENTION

The present invention relates to the field of treatment of prostate cancer and metastases thereof. More specifically, the invention relates to immunogenic polypeptides comprising at least a portion of a prostate tumour cell associated (glyco) protein or immunologically active variants thereof and to nucleic acids encoding such polypeptides. Such polypeptides and nucleic acid sequences may be used in vaccines and pharmaceutical compositions for therapeutic and prophylactic treatment of prostate cancer and metastases thereof.

BACKGROUND OF THE INVENTION

Prostate cancer is the fourth most prevalent cancer in men. In North America and Northern Europe, it is by far the most common cancer in males and is the second leading cause of cancer death in men. In the United States alone, well over 40,000 men die annually of this disease, second only to lung cancer. Despite the magnitude of these figures, there is still no effective treatment for metastatic prostate cancer. Overwhelming clinical evidence shows that human prostate cancer has the propensity to metastasize to bone, and the disease appears to progress inevitably from androgen dependent to androgen refractory status, leading to increased patient mortality.

In spite of considerable research into therapies for the disease, prostate cancer remains difficult to treat. Surgical prostatectomy, radiation therapy, hormone ablation therapy, surgical castration and chemotherapy continue to be the main treatment modalities. Unfortunately, these methods are ineffective in a significant percentage of cases. The age and underlying health of the man, the extent of metastasis, appearance under the microscope, and response of the cancer to initial treatment are important in determining the outcome of the disease and potential treatment. The decision whether or not to treat localized prostate cancer (a tumor that is contained within the prostate) with curative intent is a patient trade-off between the expected beneficial and harmful effects in terms of patient survival and quality of life.

The identification of novel therapeutic targets is essential for improving the current treatment of prostate cancer patients. Recent advances in molecular medicine have increased the interest in tumour-specific cell surface antigens that could serve as targets for various immunotherapeutic or small molecule strategies.

Among the various elements of the immune system, T lymphocytes are probably the most adept to recognize and eliminate cells expressing foreign or tumour-associated antigens. Cytotoxic T Lymphocytes (CTLs) express the CD8 cell surface marker and are specialized at inducing lysis of the target cells with which they react via the perforin/granzyme and/or the Fas/Fas-L pathways. The T-cell receptor (TCR) for antigen of CTLs binds to a molecular complex on the surface of the target cell formed by small peptides (8-11) residues derived from processed foreign or tumour associated antigens, which associate with major histocompatibility complex (MHC) class I molecules.

The other major T-cell subset, helper T lymphocytes (HTLs or T helper cells), is characterized by the expression of CD4 surface marker. The T helper cells recognize slightly larger peptides (11-20 residues), also derived from foreign or tumour associated antigens, but in the context of MHC class II molecules, which are only expressed by specialized antigen presenting cells (APCs) such as B lymphocytes, macrophages and dendritic cells (DCs).

As a consequence of TCR stimulation of naive CTLs and HTLs by peptide/MHC complexes on APCs, the CTLs mature into effector killer cells capable of lysing (tumour) cells that express the corresponding peptide/MHC class I complex. Activated HTLs amplify CTL responses by making the APCs more effective at stimulating the naive CTLs and by producing lymphokines that stimulate the maturation and proliferation of CTLs. The potentiating effect of T helper cells occurs both in secondary lymphoid organs where the immune response is initiated and at the tumor site where CTL responses need to be sustained until the tumour cells are eliminated. Thus, one would predict that vaccines should stimulate both tumour-reactive CTLs and HTLs to generate effective antitumour immunity.

Antigens suitable for immunotherapeutic cancer strategies should be highly expressed in cancer tissues and ideally not in normal adult tissues. Expression in tissues that are dispensable for life, however, may be acceptable.

SUMMARY OF THE INVENTION

The present inventors have surprisingly found that suitable antigens for immunotherapeutic strategies in the treatment of prostate cancer and metastases thereof are provided by the zona pellucida (glyco)proteins. In accordance with the invention, ZP antigens that are able to induce a $CD8^+$ and/or $CD4^+$ T cell response as well as nucleic acid sequences encoding said antigens, can suitably be used in an immunotherapeutic strategy for therapeutic and/or prophylactic treatment of prostate cancer.

The present invention resides in the finding that prostate tumour cells display significant expression of ZP (glyco) proteins, to such extent that these cells are effectively targeted by the immune response elicited by administration of ZP (glyco)protein derived antigens, resulting in decreased growth or even reduced size of primary prostatic tumours as well as of metastases originating therefrom. The present strategy is equally suitable for preventing metastasis of a prostate tumour as well as for preventing the recurrence of prostate tumours in treated subjects.

ZP3 is normally found in the so-called 'zona pellucida' that forms an extracellular matrix surrounding the developing and ovulated oocyte and the preimplantation embryo. This zona pellucida induces acrosome reaction on sperm, determines the species specificity for fertilization and prevents polyspermy in mammals. The zona pellucida contains four major glycoproteins, ZP1, ZP2, ZP3 and ZP4.

Expression of ZP (glyco)protein in prostate (derived) tumours cells has never been established before. There is thus no indication in the prior art that prostatic tumour cells can in fact become the target of a cellular immune response elicited by administering ZP (derived) antigens.

The present invention therefore provides for the first time a methods of treating prostate tumors in a human comprising immunizing said human with a source of a polypeptide comprising a class I MHC- or class II MHC-restricted native zona pellucida T cell epitope or immunologically active variants thereof, as well as to compositions suitable for use in such methods.

The present invention will be described in more detail hereafter.

DETAILED DESCRIPTION OF THE INVENTION

A first aspect of the present invention relates to a method for treatment of prostate cancer and metastases thereof in a subject by inducing a primary immune response to ZP (glyco) proteins, the method comprising the step of administering to said human a source of a polypeptide, said polypeptide comprising a class I MHC- and/or class II MHC-restricted native zona pellucida T cell epitope that is capable of eliciting a T-cell mediated immune response in vivo or an immunologically active variant thereof. In a particularly preferred embodiment of the invention, the present method is a method for therapeutic treatment.

The naming of the ZP glycoprotein components has been rather inconsistent over the years, employing several criteria, including apparent molecular weight, protein sequence length and sequence identity comparison, which has resulted in a confused nomenclature. Harris et al. [(1994) DNA seq. 96:829-834] proposed a uniform system of nomenclature in which ZP genes were named in order of length of their encoded protein sequence from longest to shortest. Since, under those criteria the mouse ZP genes fell in the order ZP2, then ZP1 and then ZP3, a new system was introduced wherein ZP2 became ZPA, ZP1, became ZPB and ZP3 became ZPC. More recently Hughes et al [(1999) BBA-Gene Structure and Expression 1447:303-306], amongst others, reported that the true human orthologue of the known mouse ZP1 gene is not ZPB, but that there is a distinct human ZP1 gene. It is now generally accepted that there are four distinct (human) ZP glycoprotein families ZP1, ZP2, ZP3 and ZPB [cf. Lefievre et al (2004) Hum. Reprod. 19:1580-1586]. The ZPB glycoprotein according to this nomenclature is now also referred to as ZP4. This nomenclature is for example applied in the Uniprot/SWISSprot, ensEMBL, BLAST (NCBI), SOURCE, SMART, STRING, PSORT2, CDART, UniGene and SOSUI databases, all implemented in the Bioinformatic Harvester (http://harvester.embl.de).

In accordance with this the terms ZP1, ZP2, ZP3 and ZP4 are employed herein to denote the four ZP glycoprotein families, wherein ZP2, ZP3 and ZP4 correspond to ZPA, ZPC and ZPB respectively according to the nomenclature proposed by Harris et al. More in particular, the terms hZP1, hZP2, hZP3 and hZP4 as used herein refer to the (glyco)proteins having polypeptide backbones of sequence protocols SEQ ID NO. 1, SEQ ID NO. 2, SEQ ID NO. 3 and SEQ ID NO. 4 respectively and allelic variants thereof.

Hence, allelic variants of the ZP1, ZP2, ZP3 and ZP4 sequences that can occur in human are also encompassed by the respective terms (h)ZP1, (h)ZP2, (h)ZP3 and (h)ZP4. Allelic variants include in particular variants resulting from single nucleotide polymorphisms (SNP's). SNP's may fall within coding sequences of genes, non-coding regions of genes, or in the intergenic regions between genes. SNPs within a coding sequence will not necessarily change the amino acid sequence of the protein that is produced. A SNP in which both forms lead to the same polypeptide sequence is termed synonymous (sometimes called a silent mutation)—if a different polypeptide sequence is produced they are non-synonymous. For a variant to be considered a SNP, it must occur in at least 1% of the population. In the context of the present invention 'allelic variants' may also include polypeptide sequence variants resulting from (nonsynonymous) mutations, i.e. polypeptide variants resulting from point mutations, insertions, deletions, etc. occurring in less than 1% of the population.

Thus, in accordance with the present invention the terms (h)ZP1, (h)ZP2, (h)ZP3 and (h)ZP4 include ZP (glyco)proteins which differ from SEQ ID NO. 1, SEQ ID NO. 2, SEQ ID NO. 3 and SEQ ID NO. 4 respectively by minor sequence modifications. Such modifications include, but are not limited to: changes in one or a few amino acids, including deletions (e.g., a truncated version of the peptide) insertions and/or substitutions. Typically, when optimally aligned, such as by the programs GAP or BESTFIT using default parameters an allelic variant shares at least a certain percentage of sequence identity with sequences referred to above. GAP uses the Needleman and Wunsch global alignment algorithm to align two sequences over their entire length, maximizing the number of matches and minimizes the number of gaps. Generally, the GAP default parameters are used, with a gap creation penalty=8 and gap extension penalty=2. For proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA. Alternatively percent similarity or identity may be determined by searching against databases such as FASTA, BLAST, etc. An 'allelic variant' is herein understood to have at least 90%, preferably at least 95%, more preferably at least 98%, still more preferably at least 98%, still more preferably at least 99%, still more preferably at least 99.5% and most preferably at least 99.9% amino acid sequence identity with any of SEQ ID NO. 1, SEQ ID NO. 2, SEQ ID NO. 3 and SEQ ID NO. 4.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The term 'prostate cancer', as used herein, refers to both primary prostate tumours as well as metastases of said primary prostate tumours that may have settled anywhere in the body.

Typically, for the purpose of the present invention, the term 'prostate cancer' or 'prostate tumour' is synonymous with 'neoplastic prostate disease' or 'prostate neoplasm'. These terms are deemed entirely interchangeable, although it is noted that for diseases of certain tissues other than the prostate, the terms 'neoplasm' and 'tumour' may be considered not to coincide entirely. In accordance with the present invention the term 'prostate cancer' typically does not include pre-neoplastic conditions, such as hyperplasia, metaplasia, dysplasia or the like.

An important aspect of the present invention is the finding of expression of ZP (glyco)protein on the prostatic (tumour) cell which allows for an immune response to be elicited against said cells. Nevertheless, as different tumours may have different or altered patterns of gene expression, certain prostatic tumours not expressing ZP (glyco)proteins to any significant extent might occur as well, as will be understood by the skilled person. Hence, typically, the invention concerns treatment of prostate cancer or metastases thereof, expressing ZP (glyco)proteins, preferably ZP3.

The method according to the invention may constitute the primary treatment or be applied as adjunctive therapy during or following treatment of patients using any of the conventional methods, including for example surgery, cryosurgery, radiation therapy, including brachytherapy and external beam radiation, High Intensity Focused Ultrasound (HIFU), hormonal therapy or chemotherapy, or some combination thereof. It is however common knowledge that many of the conventional anti-cancer treatments, especially chemotherapy and radiation can be highly immunosuppressive. It will thus be clear to the skilled person that the efficacy of the present method may be lower when following such treatments.

The invention provides methods which are suitably employed for treatment of primary prostate cancer and metastases thereof, which is considered herein to constitute 'therapeutic treatment' or 'curative treatment', as well as for preventing metastases and/or recurrence of prostate cancer optionally after or in combination with other methods of treatment, such as described before, which is considered herein to constitute 'prophylactic treatment'. In a particularly preferred embodiment of the invention the method according to the invention is applied in combination with surgery, hormonal therapy and/or treatment with an agent selected from docetaxel, bevacizumab, thalidome, cabzitaxel, abiraterone, temozolomide.

For the methods of the invention, the subject to be treated is preferably a human male.

In accordance with the present invention, the 'source of a polypeptide' that is administered to the human according to the present method, may be or comprise a protein or glycoprotein, a digest of the protein or glycoprotein and/or fragments thereof, which may be in a purified form or may be comprised within a crude composition, preferably of biological origin, such as lysates, sonicates or fixates of prokaryotic or eukaryotic cell lines. Alternatively, said source of a polypeptide may be or comprise chemically synthesized (poly)peptides or (poly)peptides that have been produced enzymatically in vitro, which may be in a purified form or may be comprised within a crude composition. The source of the polypeptide may also be or comprise a nucleic acid encoding the polypeptide, from an RNA or DNA template. The RNA or DNA molecules may be 'naked' DNA, preferably comprised in vesicles or liposomes, or may be comprised in a vector. The vector may be any (recombinant) DNA or RNA vector known in the art, and preferably is a plasmid wherein genes encoding latency antigens are operably linked to regulatory sequences conferring expression and translation of the encoded messengers. The vector may also be any DNA or RNA virus, such as but not limited to Adenovirus, Adeno-Associated Virus (AAV), a retrovirus, a lentivirus, modified Vaccinia Ankara virus (MVA) or Fowl Pox virus, or any other viral vector capable of conferring expression of polypeptides comprising latency epitopes to a host. DNA vectors may be non-integrating, such as episomally replicating vectors or may be vectors integrating in the host genome by random integration or by homologous recombination. An example of the construction of plasmids incorporating human ZP2 cDNA, which plasmids could suitably be used in accordance with the present invention can be found in a publication by Martinez et al. [(1996) Journal of Reproduction and Fertility Supplement 50:35-41], which is incorporated herein by reference.

DNA molecules comprising genes encoding the polypeptides according to the current invention, optionally embedded in vectors such as viruses or plasmids, may be integrated in a genome of a host. In a preferred embodiment of the invention, such a host may be a micro-organism. Preferably such a recombinant micro-organism is a *Mycobacterium*, for instance of the species *M. tuberculosis* or *M. bovis* and most preferably *M. bovis* Bacillus Calmette Guerin (BCG), capable of delivering to a host the polypeptides or fragments thereof according to the invention. Recombinant BCG and methods for recombination are known in the art, for instance in WO2004094469. Such a recombinant micro-organism may be formulated as a live recombinant and/or live attenuated vaccine, as for instance in Jacobs et al. 1987, Nature, 327(6122):532-5). The vector may also be comprised in a host of bacterial origin, such as but not limited to live-attenuated and/or recombinant *Shigella* or *Salmonella* bacteria.

The term "epitope" as used herein refers to a portion of an antigen, typically defined by a peptide, which is capable of eliciting a cellular or humoral immune response when presented in a physiologically relevant context in vivo. A "T cell epitope" refers to a peptide or portion thereof that binds to an MHC molecule and is recognized by T cells when presented in MHC molecules. A T cell epitope is capable of inducing a cell mediated immune response via direct or indirect presentation in heterodimeric membrane MHC molecules. Briefly, MHC molecules preferentially bind particular amino acid residues known as "anchor" residues (K. Falk et al., Nature 351:290-96 (1991)). This characterization permits class I and II MHC recognition epitopes to be identified within any known peptide sequence. In the present context, the term "MHC restricted epitope" is synonymous with T cell epitope. The term "class I MHC restricted epitope", as used herein, refers to peptide sequences recognized by cytotoxic T lymphocytes (also called $CD8^+$ cells or CTLs) in association with class I MHC. The term "class II MHC restricted epitope", as used herein, refers to a peptide recognized by helper T cells (also called $CD4^+$ cells or HTLs). A "B cell epitope" is a portion of an antigen, typically a peptide, capable of binding to an antigen binding site of an immunoglobulin and therefore capable of stimulating a humoral response without presentation in an MHC molecule. As explained herein before the polypeptide useful in the present invention, or the nucleic acid encoding said polypeptide, comprises at least one T cell epitope. The use of polypeptides that also comprise a B cell epitope is however not excluded from the present invention. The present immunogenic polypeptides may also include multiple T cell epitopes and, optionally a B cell epitope. When multiple epitopes are present in a peptide, the epitopes may be oriented in tandem or in a nested or overlapping configuration wherein at least one amino acid residue may be shared by two or more epitopes.

The polypeptide of the invention preferably includes one or more MHC class I binding epitopes. As is generally known by the skilled person, an antigen comprising a single peptide epitope will be useful only for treating a (small) subset of patients who express the MHC allele product that is capable of binding that specific peptide. It has been calculated that, in humans, vaccines containing CTL epitopes restricted by HLA-A1, -A2, -A3, -A24 and -B7 would offer coverage to approximately 80% of individuals of most ethnic backgrounds. Therefore, if the present method is used to treat a human male, it is particularly preferred that the present source of a polypeptide comprises an effective amount of one or more different polypeptides comprising one, more preferably two, most preferably three MHC class I binding native ZP epitopes selected from HLA-A1, HLA-A2, HLA-A3, HLA-A24 and HLA-B7 restricted epitopes; or homologues thereof or one or more nucleic acid sequence encoding said one or more polypeptides or homologues thereof.

According to another embodiment the polypeptide of the invention preferably includes one or more MHC class II binding epitopes. The most frequently found MHC class II allele products in humans include HLA-DR1, -DR3, -DR4 and -DR7. Accordingly, it is preferred that the present source of a polypeptide comprises an effective amount of one or more different polypeptides, said one or more different polypeptides comprising one, more preferably two and most preferably three MHC class II binding native ZP epitopes selected from HLA-DR1, HLA-DR3, HLA-DR4 and HLA-DR7 restricted epitopes; or homologues thereof or one or more nucleic acid sequence encoding said one or more polypeptides or homologues thereof.

In still another embodiment, the present source of a polypeptide comprises an effective amount of one or more polypeptides, said one or more polypeptides comprising one or more MHC class I binding epitopes and one or more MCH class II binding epitopes, as described here above; homologues thereof or one or more nucleic acid sequence encoding said polypeptides or homologues thereof. Even, more preferably said source comprises an effective amount of one or more different polypeptides that together include essentially all of the MHC class I and MHC class II binding epitopes comprised in one of the native ZP glycoproteins; or homologues of said one or more polypeptides or one or more nucleic acid sequence encoding said polypeptides or homologues thereof.

In one embodiment, the present source of a polypeptide comprises an effective amount of one or more different immunogenic polypeptides, which one or more different polypeptides together comprise at least 50%, more preferably at least 70%, still more preferably at least 80%, still more preferably at least 90% and most preferably at least 95% of the MHC class I and MHC class II restricted binding epitopes comprised in a native ZP glycoprotein; or homologues of said one or more polypeptides or one or more nucleic acid sequences encoding them.

In a preferred embodiment the present source of a polypeptide comprises an effective amount of an immunogenic polypeptide, which polypeptide comprises at least 50%, more preferably at least 70%, still more preferably at least 80%, still more preferably at least 90% and most preferably at least 95% of the complete amino acid backbone of a ZP glycoprotein, preferably hZP; or a homologue of said polypeptide or a nucleic acid sequence encoding said polypeptide or homologue thereof.

In another particularly preferred embodiment, the source of a polypeptide comprises an effective amount of a plurality of different overlapping polypeptide fragments of a ZP glycoprotein, preferably hZP, which different overlapping polypeptide fragments are between 18-60 amino acids in length, preferably 18-45 amino acids, and which together comprise at least 50%, more preferably at least 70%, still more preferably at least 80%, still more preferably at least 90% and most preferably at least 95% of the complete amino acid backbone of said ZP glycoproteins; homologues of said polypeptides or one or more nucleic acid sequences encoding said polypeptides or homologues thereof. Typically, the amino acid overlap between the different consecutive 16-80 amino acid polypeptide fragments is at least 7 amino acids, preferably at least 8, more preferably at least 9 and most preferably at least 10 amino acids.

The MHC binding motifs for most common MHC class I and II alleles have been described. These motifs itemize the amino acid residues that serve as MHC binding anchors for specific class I and class II MHC alleles. Sophisticated computer-based algorithms that take into account the MHC binding anchors as well as the amino acids sequence of a peptide are used to predict and quantify the binding affinity of the peptide/MHC interaction. Thus, from the input of the known amino acid sequence of Zona Pellucida (glyco)proteins, these algorithms list all potential T-cell epitopes, each with its corresponding predictive binding score. Commonly known bio-informatics tools for these purposes include HLA_BIND, SYFPEITHI, NetMHC and TEPITOPE 2000 [see references 1-6]. Alternatively, the skilled artesian will be able to determine HTL and CTL binding epitopes experimentally using standard experimentation (Current Protocols in Immunology, Wiley Interscience 2004).

In some cases it has been observed that the same peptide may bind to several MHC I or II allele products. In one embodiment, the use of such 'promiscuous' MHC binding peptides in the present method is particularly preferred.

In one embodiment, the current invention provides a method for the induction of a primary immune response to native Zona Pellucida glycoproteins in a human male, wherein the method comprises the step of administering to the human a source of a polypeptide, said polypeptide comprising a class I MHC- and/or class II MHC-restricted native zona pellucida T cell epitope or an immunologically active variant thereof, wherein said source of a polypeptide comprises an effective amount of an immunogenic polypeptide selected from Zona Pellucida (glyco)proteins, homologues thereof, and immunologically active fragments of said (glyco)proteins and homologues thereof; or a nucleic acid sequence encoding said immunogenic polypeptide. According to a preferred embodiment said Zona Pellucida (glyco)protein is selected from the group of ZP1, ZP2, ZP3 and ZP4, more preferably ZP2 and ZP3, most preferably ZP3.

According to one particularly preferred embodiment, the source of a polypeptide comprises an effective amount of an immunogenic polypeptide selected from human Zona Pellucida (glyco)proteins, homologues thereof and immunologically active fragments of these (glyco)proteins and their homologues, or a nucleic acid sequence encoding said immunogenic polypeptide. Preferably said human Zona Pellucida (glyco)protein (hZP (glyco)protein) is selected from the group of hZP1, hZP2, hZP3 and hZP4. According to an even more preferred embodiment said (glyco)protein is selected from the group of hZP2 and hZP3, more preferably said (glyco)protein is hZP3.

The term 'immunologically active fragments thereof' will generally be understood in the art to refer to a fragment of a polypeptide antigen comprising at least an epitope, which means that the fragment at least comprises 4, 5, 6, 7 or 8 contiguous amino acids from the sequence of the polypeptide antigen. According to the present invention the fragment comprises at least a T cell epitope. Thus an 'immunologically active fragment' according to this invention comprises at least 8, 9, 10, 11, 12, 13, or 14 contiguous amino acids from the sequence of the ZP (glyco)protein antigen or homologue or analogue thereof. Still more preferably the fragment comprises both a CTL and a T helper epitope. Most preferably however, the fragment is a peptide that requires processing by an antigen presenting cell, i.e. the fragment has a length of at least about 18 amino acids, which 18 amino acids are not necessarily a contiguous sequence from the polypeptide antigen.

The terms 'homologues thereof', as used herein refer to polypeptides which differ from the naturally occurring polypeptide by minor modifications, but which maintain the basic polypeptide and side chain structure of the naturally occurring form. Such changes include, but are not limited to: changes in one or a few amino acid side chains; changes in one or a few amino acids, including deletions (e.g., a truncated version of the peptide) insertions and/or substitutions; changes in stereochemistry of one or a few atoms; additional N- or C-terminal amino acids; and/or minor derivatizations, including but not limited to: methylation, glycosylation, phosphorylation, acetylation, myristoylation, prenylation, palmitation, amidation and/or addition of glycosylphosphatidyl inositol. As used herein, a homologue or analogue has either enhanced or substantially similar functionality as the naturally occurring polypeptide.

A homologue herein is understood to comprise an immunogenic polypeptide having at least 70%, preferably at least 80%, more preferably at least 90%, still more preferably at least 95%, still more preferably at least 98% and most preferably at least 99% amino acid sequence identity with the naturally occurring ZP3 polypeptides of the invention, when optimally aligned, such as by the programs GAP or BESTFIT using default parameters, and is still capable of eliciting at least the immune response obtainable thereby. Generally, the GAP default parameters are used, with a gap creation penalty=8 and gap extension penalty=2. For proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752, USA. Alternatively percent similarity or identity may be determined by searching against databases such as FASTA, BLAST, etc.

According to an embodiment of the invention, the present immunogenic polypeptides as defined herein before, are glycosylated. Without wishing to be bound by theory it is hypothesized that by glycosylation of these polypeptides the immunogenicity thereof is increased. Therefore, according to a preferred embodiment, the aforementioned immunogenic polypeptide as defined herein before, is glycosylated, having a carbohydrate content varying from 10-80 wt %, based on the total weight of the glycoprotein or glycosylated polypeptide. More preferably said carbohydrate content ranges from 15-70 wt %, still more preferably from 20-60 wt %. In another embodiment, said glycosylated immunogenic polypeptide comprises a glycosylation pattern that is similar to that of the corresponding zona pellucida glycoprotein (or fragment thereof) of a human. It is hypothesized that this even further increases the immunogenicity of said polypeptide. Thus, in an embodiment it is preferred that the immunogenic polypeptide comprises a glycosylation pattern that is similar to that of the corresponding (fragment of) human ZP glycoprotein. Nevertheless, as is known by the skilled person, recombinant techniques for the production of the immunogenic polypeptide may yield polypeptides which are not glycosylated or which contain different glycosylation patterns, depending on inter alia the choice of the host cells, as will be explained herein below. It will be clear to the skilled person, that the use of recombinant polypeptides, having glycosylation patterns dissimilar to that of the corresponding hZP (fragment), is also entirely within the scope of the present invention and might be preferred in certain embodiments, e.g. for practical reasons.

The present method of immunization preferably comprises the administration of a source of immunogenically active polypeptide fragments, said polypeptide fragments being selected from Zona Pellucida protein fragments and/or homologues thereof as defined herein before, said polypeptide fragments comprising dominant CTL and/or HTL epitopes and which fragments are between 18 and 45 amino acids in length. Peptides having a length between 18 and 45 amino acids have been observed to provide superior immunogenic properties as is described in WO 02/070006. Peptides may advantageously be chemically synthesized and may optionally be (partially) overlapping and/or may also be ligated to other molecules, peptides or proteins. Peptides may also be fused to form synthetic proteins, as in PCT/NL03/00929 and in Welters et al. (Vaccine. 2004 Dec. 2; 23(3):305-11). It may also be advantageous to add to the amino- or carboxy-terminus of the peptide chemical moieties or additional (modified or D-) amino acids in order to increase the stability and/or decrease the biodegradability of the peptide. To improve the immunogenicity/immuno-stimulating moieties may be attached, e.g. by lipidation or glycosylation. To enhance the solubility of the peptide, addition of charged or polar amino acids may be used, in order to enhance solubility and increase stability in vivo.

For immunization purposes the aforementioned immunogenic polypeptides according to the invention may also be fused with proteins such as but not limited to tetanus toxin/toxoid, diphtheria toxin/toxoid or other carrier molecules. The polypeptides according to the invention may also be advantageously fused to heatshock proteins, such as recombinant endogenous (murine) gp96 (GRP94) as a carrier for immunodominant peptides as described in (references: Rapp U K and Kaufmann S H, Int Immunol. 2004 April; 16(4):597-605; Zugel U, Infect Immun. 2001 June; 69(6):4164-7) or fusion proteins with Hsp70 (Triebel et al; WO9954464).

The individual amino acid residues of the present immunogenic (poly)peptides of the invention can be incorporated in the peptide by a peptide bond or peptide bond mimetic. A peptide bond mimetic of the invention includes peptide backbone modifications well known to those skilled in the art. Such modifications include modifications of the amide nitrogen, the α-carbon, amide carbonyl, complete replacement of the amide bond, extensions, deletions or backbone cross-links. See, generally, Spatola, Chemistry and Biochemistry of Amino Acids, Peptides and Proteins, Vol. VII (Weinstein ed., 1983). Several peptide backbone modifications are known, these include, ψ [$CH_2S$], ψ [$CH_2NH$], ψ [$CSNH_2$], ψ [NHCO], ψ [$COCH_2$] and ψ [(E) or (Z) CH=CH]. The nomenclature used above, follows that suggested by Spatola, above. In this context, ψ indicates the absence of an amide bond. The structure that replaces the amide group is specified within the brackets.

Amino acid mimetics may also be incorporated in the polypeptides. An "amino acid mimetic" as used here is a moiety other than a naturally occurring amino acid that conformationally and functionally serves as a substitute for an amino acid in a polypeptide of the present invention. Such a moiety serves as a substitute for an amino acid residue if it does not interfere with the ability of the peptide to elicit an immune response against the native ZP T cell epitopes. Amino acid mimetics may include non-protein amino acids, such as β-, γ-, δ-amino acids, β-, γ-, δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, (1989) Ann. Repts. Med. Chem. 24:243-252.

According to a preferred embodiment, the present method comprises the administration of a composition comprising one or more of the present immunogenic polypeptides as defined herein above, and at least one excipient. Excipients are well known in the art of pharmacy and may for instance be found in textbooks such as Remmington's pharmaceutical sciences, Mack Publishing, 1995.

The present method for immunization may further comprise the administration, preferably the co-administration, of at least one adjuvant. Adjuvants may comprise any adjuvant known in the art of vaccination and may be selected using textbooks like Current Protocols in Immunology, Wiley Interscience, 2004.

Adjuvants are herein intended to include any substance or compound that, when used, in combination with an antigen, to immunise a human or an animal, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a human, thereby excluding immunostimulatory compounds that are endogenous to humans, such as e.g. interleukins, interferons and other hormones.

A number of adjuvants are well known to one skilled in the art. Suitable adjuvants include e.g. incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxy-phosphoryloxy)-ethylamine (CGP 19835A, referred to as MTP-PE), DDA (2 dimethyldioctadecylammonium bromide), polyIC, Poly-A-poly-U, RIBI™, GERBU™, Pam3™, Carbopol™, Specol™, Titermax™, tetanus toxoid, diphtheria toxoid, meningococcal outer membrane proteins, diphtheria protein $CRM_{197}$. Preferred adjuvants comprise a ligand that is recognised by a Toll-like-receptor (TLR) present on antigen presenting cells. Various ligands recognised by TLR's are known in the art and include e.g. lipopeptides (see e.g. WO 04/110486), lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications.

The present method for immunization may further comprise the administration, preferably the co-administration, of a CD40 binding molecule in order to enhance a CTL response and thereby enhance the therapeutic effects of the methods and compositions of the invention. The use of CD40 binding molecules is described in WO 99/61065, incorporated herein by reference. The CD40 binding molecule is preferably an antibody or fragment thereof or a CD40 Ligand or a variant thereof, and may be added separately or may be comprised within a composition according to the current invention. For therapeutic applications, the present immunogenic polypeptides or nucleic acid sequences encoding them or the present compositions comprising these polypeptides or nucleic acid sequences encoding them are administered to a patient suffering from a prostate tumour and possibly metastases thereof or to a patient that has received other methods of treating prostate tumours, e.g. any of the conventional methods described herein before, in an amount sufficient to induce a primary autoimmune response directed against native ZP glycoproteins and tissue cells expressing ZP glycoproteins. An amount sufficient to accomplish this is defined as a "therapeutically-" or "prophylactically-effective dose". Such effective dosages will depend on a variety of factors including the condition and general state of health of the patient. Thus dosage regimens can be determined and adjusted by trained medical personnel to provide the optimum therapeutic or prophylactic effect.

In the present method the one or more immunogenic polypeptides are typically administered at a dosage of about 1 μg/kg patient body weight or more at least once. Often dosages are greater than 10 μg/kg. According to the present invention the dosages preferably range from 1 μg/kg to 1 mg/kg.

According to one preferred embodiment typical dosage regimens comprise administering a dosage of 1-1000 μg/kg, more preferably 10-500 μg/kg, still more preferably 10-150 μg/kg, once, twice or three times a week for a period of one, two, three, four or five weeks. According to a preferred embodiment 10-100 μg/kg is administered once a week for a period of one or two weeks.

The present method preferably comprises administration of the present immunogenic polypeptides and compositions comprising them via the parenteral or oral route, preferably the parenteral route.

Another embodiment of the invention comprises ex vivo administration of a composition comprising the present immunogenic peptides to mononuclear cells from the patients blood, particularly DC isolated therefrom. A pharmaceutical to facilitate harvesting of DC can be used, such as Progenipoietin™ (Monsanto, St. Louis, Mo.) or GM-CSF/IL-4. After pulsing the DC with peptides and washing to remove unbound peptides, the DC are reinfused into the patient. In this embodiment, a composition is provided comprising peptide-pulsed DC which present the pulsed peptide epitopes in HLA molecules on their surfaces. Methods of inducing an immune response employing ex vivo peptide-pulsed DC are well known to the skilled person.

Another aspect of the invention relates to a pharmaceutical preparation comprising as the active ingredient the present source of a polypeptide as defined herein before. More particularly pharmaceutical preparation comprises as the active ingredient one or more of the aforementioned immunogenic polypeptides selected from the group of ZP proteins, homologues thereof and fragments of said ZP proteins and homologues thereof, or, alternatively, a gene therapy vector as defined herein above.

According to a first embodiment a pharmaceutical preparation is provided comprising one or more of the immunogenic polypeptides of the invention. The concentration of said polypeptide in the pharmaceutical composition can vary widely, i.e., from less than about 0.1% by weight, usually being at least about 1% by weight to as much as 20% by weight or more.

The composition preferably at least comprises a pharmaceutically acceptable carrier in addition to the active ingredient. The pharmaceutical carrier can be any compatible, non-toxic substance suitable to deliver the immunogenic polypeptides or gene therapy vectors to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

According to a particularly preferred embodiment, the present pharmaceutical composition comprises an adjuvant, as defined in more detail herein before. Adjuvants for incorporation in the present composition are preferably selected from the group of ligands that are recognised by a Toll-like-receptor (TLR) present on antigen presenting cells, including lipopeptides (see e.g. WO 04/110486), lipopolysaccharides, peptidoglycans, liopteichoic acids, lipoarabinomannans, lipoproteins (from mycoplasma or spirochetes), double-stranded RNA (poly I:C), unmethylated DNA, flagellin, CpG-containing DNA, and imidazoquinolines, as well derivatives of these ligands having chemical modifications. The skilled person will be able to determine the exact amounts of anyone of these adjuvants to be incorporated in the present pharmaceutical preparations in order to render them sufficiently immunogenic. According to another preferred embodiment, the present pharmaceutical preparation may comprise one or more additional ingredients that are used to enhance CTL immunity as explained herein before. According to a particularly preferred embodiment the present pharmaceutical preparation comprises a CD40 binding molecule.

Methods of producing pharmaceutical compositions comprising polypeptides are described in U.S. Pat. Nos. 5,789, 543 and 6,207,718. The preferred form depends on the intended mode of administration and therapeutic application.

For gene therapy, vectors, e.g. a plasmid, phagemid, phage, cosmid, virus, retrovirus, episome or transposable element, comprising a nucleic acid sequence encoding an immunogenic polypeptide as defined herein before may be incorporated into pharmaceutical compositions. Gene therapy vectors can be delivered to a subject by, for example, intravenous injection, local administration (see U.S. Pat. No. 5,328,470) or by stereotactic injection (see e.g., Chen et al., PNAS 91:3054-3057, 1994). The pharmaceutical composition of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The present immunogenic polypeptides are preferably administered parentally. The polypeptides for preparations for parental administration must be sterile. Sterilisation is readily accomplished by filtration through sterile filtration membranes, prior to or following lyophilisation and reconstitution. The parental route for administration of the polypeptide is in accordance with known methods, e.g. injection or infusion by intravenous, intraperitoneal, intramuscular, intra-arterial, subcutaneous or intralesional routes. The polypeptide is administered continuously by infusion or by bolus injection. A typical composition for intravenous infusion could be made up to contain 10 to 50 ml of sterile 0.9% NaCl or 5% glucose optionally supplemented with a 20% albumin solution and between 10 µg and 50 mg, preferably between 50 µg and 10 mg, of the polypeptide. A typical pharmaceutical composition for intramuscular injection would be made up to contain, for example, 1-10 ml of sterile buffered water and between 10 µg and 50 mg, preferably between 50 µg and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable colour, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain colouring and flavouring to increase patient acceptance.

The immunogenic polypeptides for use in the present invention can be prepared using recombinant techniques in which a nucleotide sequence encoding the polypeptide of interest is expressed in suitable host cells such as described in Ausubel et al., "Current Protocols in Molecular Biology", Greene Publishing and Wiley-Interscience, New York (1987) and in Sambrook and Russell (2001) "Molecular Cloning: A Laboratory Manual ($3^{rd}$ edition), Cold Spring Harbor Laboratory, Cold Spring Harbor Laboratory Press, New York; both of which are incorporated herein by reference in their entirety. Also see, Kunkel (1985) Proc. Natl. Acad. Sci. 82:488 (describing site directed mutagenesis) and Roberts et al. (1987) Nature 328:731-734 or Wells, J. A., et al. (1985) Gene 34:315 (describing cassette mutagenesis).

An example of the preparation of recombinant human ZPA and ZPB, using baculoviruses can be found in the aforementioned publication by Martinez et al. [(1996) Journal of Reproduction and Fertility Supplement 50:35-41].

Examples of the preparation of recombinant human ZPA and ZPB, using bacteria (E. coli), yeast cells (Pichia pastoris), insect cells (Autographa californica multiple nuclear polyhedrosis virus) and Chinese Hamster ovary cells (CHO) as expression systems are disclosed in a publication by Harris et al. [(1999) Protein Expression and Purification 16:298-307], which is incorporated herein by reference.

An aspect of the invention thus relates to a vector comprising a nucleic acid molecule encoding the present immunogenic polypeptide as defined herein before. Preferably the vector is a replicative vector comprising an origin of replication (or autonomously replication sequence) that ensures multiplication of the vector in a suitable host for the vector. Alternatively the vector is capable of integrating into the host cell's genome, e.g. through homologous recombination or otherwise. A particularly preferred vector is an expression vector wherein a nucleotide sequence encoding a polypeptide as defined above, is operably linked to a promoter capable of directing expression of the coding sequence in a host cell for the vector.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is only active in specific types of differentiated cells/tissues.

Expression vectors allow the immunogenic polypeptides as defined above to be prepared using recombinant techniques in which a nucleotide sequence encoding the polypeptide of interest is expressed in suitable cells, e.g. cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel (1985) Proc. Natl. Acad. Sci. 82:488 (describing site directed mutagenesis) and Roberts et al. (1987) Nature 328: 731-734 or Wells, J. A., et al. (1985) Gene 34:315 (describing cassette mutagenesis).

Typically, nucleic acids encoding the desired polypeptides are used in expression vectors. The phrase "expression vector" generally refers to nucleotide sequences that are capable of affecting expression of a gene in hosts compatible with such sequences. These expression vectors typically include at least suitable promoter sequences and optionally, transcription termination signals. Additional factors necessary or helpful in effecting expression can also be used as described herein. DNA encoding a polypeptide is incorporated into DNA constructs capable of introduction into and expression in an in vitro cell culture. Specifically, DNA constructs are suitable for replication in a prokaryotic host, such as bacteria, e.g., E. coli, or can be introduced into a cultured mammalian, plant, insect, e.g., Sf9, yeast, fungi or other eukaryotic cell lines.

DNA constructs prepared for introduction into a particular host typically include a replication system recognised by the host, the intended DNA segment encoding the desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters or linkers inserted in lieu thereof.

The selection of an appropriate promoter sequence generally depends upon the host cell selected for the expression of the DNA segment. Examples of suitable promoter sequences include prokaryotic, and eukaryotic promoters well known in the art (see, e.g. Sambrook and Russell, 2001, supra). The transcriptional regulatory sequences typically include a heterologous enhancer or promoter that is recognised by the host. The selection of an appropriate promoter depends upon the host, but promoters such as the trp, lac and phage promoters, tRNA promoters and glycolytic enzyme promoters are known and available (see, e.g. Sambrook and Russell, 2001, supra). Expression vectors include the replication system and transcriptional and translational regulatory sequences together with the insertion site for the polypeptide encoding segment can be employed. Examples of workable combinations of cell lines and expression vectors are described in Sambrook and Russell (2001, supra) and in Metzger et al. (1988) Nature 334: 31-36. For example, suitable expression vectors can be expressed in, yeast, e.g. S. cerevisiae, e.g., insect cells, e.g., Sf9 cells, mammalian cells, e.g., CHO cells and bacterial cells, e.g., E. coli. Since prokaryotes do not possess the organelles necessary for glycosylation, polypeptides produced by prokaryotes will not have carbohydrate side chains. Eukaryotes do have the glycosylation machinery, but yeast cells will give a different glycosylation pattern than mammalian cells. It is therefore preferred to use an expression system which gives the most "natural" glycosylation pattern. Towards this end mammalian cells are most preferred. Cell lines having glycosylation machinery similar to that of a human can be particularly useful, since it is hypothesized that antigens according to the present invention having a glcyocylation pattern similar to that of the corresponding human Zona Pellucida glycopolypeptides may have increased immunogenicity. Suitable cell lines include CHO cells, see, e.g., U.S. Pat. No. 5,272,070 and in particular human ovary or follicle cell lines, cf. WO 99/42581.

In vitro mutagenesis and expression of mutant proteins are described generally in Ausubel et al. (1987, supra) and in Sambrook and Russell (2001, supra). Also see, Kunkel (1985, supra; describing site directed mutagenesis) and Roberts et al. (1987, supra; describing cassette mutagenesis).

Another method for preparing the present immunogenic polypeptides is to employ an in vitro transcription/translation system. DNA encoding a polypeptide is cloned into an expression vector as described supra. The expression vector is then transcribed and translated in vitro. The translation product can be used directly or first purified. Polypeptides resulting from in vitro translation typically do not contain the post-translation modifications present on polypeptides synthesised in vivo, although due to the inherent presence of microsomes some post-translational modification may occur. Methods for synthesis of polypeptides by in vitro translation are described by, for example, Berger & Kimmel, Methods in Enzymology, Volume 152, Guide to Molecular Cloning Techniques, Academic Press, Inc., San Diego, Calif., 1987 (incorporated herein by reference in its entirety).

A further aspect of the invention thus relates to a host comprising a vector as defined above. The host cells may be prokaryotic or eukarotic host cells as indicated above. The host cell may be a host cell that is suitable for culture in liquid or on solid media. Alternatively, the host cell is a cell that is part of a multicellular organism such as a transgenic plant or animal, preferably a non-human animal.

A further aspect the invention relates to a method for producing the present immunogenic polypeptide as defined above. The method comprises the step of culturing a host cell as defined above under conditions conducive to the expression of the polypeptide. Optionally the method may comprise recovery the polypeptide. The polypeptide may e.g. be recovered from the culture medium by standard protein purification techniques, including a variety of chromatography methods known in the art per se.

Another aspect of the invention relates to a transgenic animal comprising in its somatic and germ cells a vector as defined above. The transgenic animal preferably is a non-human animal. Methods for generating transgenic animals are e.g. described in WO 01/57079 and in the references cited therein. Such transgenic animals may be used in a method for producing a polypeptide as defined above, the method comprising the step of recovering a body fluid from a transgenic animal comprising the vector or a female descendant thereof, wherein the body fluid contains the polypeptide, and, optionally recovery of the polypeptide from the body fluid. Such methods are also described in WO 01/57079 and in the references cited therein. The body fluid containing the polypeptide preferably is blood or more preferably milk.

Yet another aspect of the invention relates to a transgenic plant comprising in its cells a vector as defined above. Methods for generating transgenic plants are e.g. described in U.S. Pat. No. 6,359,196 and in the references cited therein. Such transgenic plants may be used in a method for producing a polypeptide as defined above, the method comprising the step of recovering a part of a transgenic plant comprising in its cells the vector or a part of a descendant of such transgenic plant, whereby the plant part contains the polypeptide, and, optionally recovery of the polypeptide from the plant part. Such methods are also described in U.S. Pat. No. 6,359,196 and in the references cited therein.

The invention is further illustrated in the following examples, which are not intended to limit the scope of the invention in any manner.

EXAMPLES

Experiment 1

Expression of ZP3 in Human Prostate Carcinoma Samples

The expression of ZP3 in human prostate tumour tissue is determined using immunohistochemical methods. Samples from prostate tumour tissues originating from different patients were obtained from a pathology institute in the Netherlands. In total 16 human prostate carcinoma samples and 6 other prostate tumor samples from other different sources were stained for ZP3 (IHC & IF), alpha-methyl-CoA-Racemase AMACR (a prostate carcinoma IHC marker as 85% of all prostate cancer stains for them) and Cytokeratin 5/6 (for basal cells).

Immunohistochemical determinations were done with human ZP3 antibodies, rabbit polyclonal antibodies to human recombinant ZP3 and with goat polyclonal antibodies.

Samples of normal prostate tissue served as control. Immature oocytes collected from antral follicles following ovarian stimulation for IVF were stained as positive controls. In addition, a samples of normal liver and normal testis tissue were used as a negative controls.

The following IHC protocol was used for all samples

Day 1
1. Incubation slides in 57° C. for 30 min.
2. Deparaffinization and hydration:
   a) Xylene—2×5 min,
   b) Abs. EtOH—2×5 min,
   c) 96% EtOH—2×5 min,
   d) 70% EtOH—2×5 min, e) 50% EtOH—2×5 min,
   f) dH20—1×5 min, g) PBS—1×5 min.
3. Antigen retrieval:
   a) 10 mM sodium citrate buffer (pH 6.0) in microwave oven for 15 min,
   b) Cool for 15-20 min,
   c) PBS—3×5 min.
4. Quenching of endogenous peroxidase (RT in dark, 3% H2O2 in methanol—10 min recommended for paraffin sections)
5. PBS—3×5 min.
6. Blocking—NGS 15% in TPBS—90 min (RT in dark/humidified chamber).
7. Primary antibody 1:250 with 5% NGS in TPBS—over night/cold room/humidified chamber).

For positive control (WT ovary) 1:600 diluted primary antibody was used. For tumour sections antibody was more concentrated—1:250.

Day 2
8. PBS—3×5 min.
9. Secondary antibody—goat anti-rabbit (1:1000) with 5% NGS in TPBS—90 min (RT/humidified chamber).
10. PBS—3×5 min
11. Incubation with ABC-Reagent diluted 1:50 in PBS (60 min/RT in dark/humidified chamber).
12. PBS—3×5 min.
13. DBA
14. Aqua—2×5 min.
15. Hematoxilin—60 s.
16. Aqua—2×5 min.
17. Dehydration:
    a) 50% EtOH—2×5 min
    b) 70% EtOH—2×5 min
    c) 96% EtOH—2×5 min
    d) Abs. EtOH—2×5 min
    e) Xylene—2×5 min (ultra clear)
18. Mount with DPX.

Cells (50.000) were seeded each time on cover glasses (which are usually used for IHC). After 24 h or less (depending on the cell line) cells were washed with PBS and fixed with 4% PFA (15 min). Then cells were washed again with PBS (3×5 min). After washing autofluorescence was blocked with 100 mM $NH_4Cl$ (3 min RT). In the next step 15% NGS was used in combination with 5% BSA in PBS with 0.1% Triton X-100 (90 min/RT/humidified chamber). Primary antibody was diluted 1:200 (can be higher) in 5% NGS in T-PBS (over night/cold room/humidified chamber). After incubation with primary antibody cells were washed (3×5 min, T-PBS) and incubated with secondary antibody AlexaFluor 594 (goat anti-rabbit) diluted 1:100 (90 min/RT/humidified chamber). Finally cells were washed (3×5 min; PBS) and counterstained (DAPI-Ultra Cruz).

Solutions and Reagents
  Xylene (or Histoclear)
  Ethanol
  Distilled $H_2O$
  Haematoxylin
  10×PBS (Phosphate Buffered Saline):
    0.58 M sodium phosphate dibasic ($Na_2HPO_4$), 0.17 M sodium phosphate monobasic ($NaH_2PO_4$), 0.68 M NaCl. To prepare 1 liter of 10×PBS: Combine 82.33 g $Na_2HPO_4*4H_2O$, 23.45 g $NaH_2PO_4*H_2O$ and 40 g NaCl. Adjust pH to 7.4.
  10 mM Sodium Citrate Buffer:
  To prepare 1 liter, add 2.94 g sodium citrate to 1 liter $dH_2O$. Adjust pH to 6.0
  1% Hydrogen Peroxide (oxidation) buffer:
  In 50 ml: 15 µl Triton-X, 10 ml Methanol, 40 ml 1% $H_2O_2$ (final conc.)
  Blocking solution:
  10% FBS and 10% BSA in PBS
  ABC reagent (Vectastain ABC kit, Vector laboratories, Inc., Burlingame, Calif.):
  Prepare acoording to manufacturer's instructions 30 minutes before use
  DAB reagent:
  Use as per manufacturer's instructions In the positive controls, antibodies detect proteins in the ZP surrounding the human oocyte (results not shown). ZP3 proteins are also present in the oocyte cytoplasm. No positive staining is detected in sections of the prostate tumour tissue samples when the primary antibody is omitted (results not shown). No positive staining is observed, with each of the ZP antibodies, in liver tissue (results not shown), normal prostate or normal human testis (FIGS. 3C and 3D respectively).

In the prostate tumour samples, presence of the ZP3 is confirmed by areas of the tissue staining positive for ZP3, with intensities varying among the samples obtained from different patients (FIGS. 3A and 3B).

Overall, ZP3 positive staining correlated strictly with prostate cancer marker alpha-methyl-CoA-Racemase (AMACR) for the prostate carcinoma.

These tumours staining positive for ZP3 expression can be treated by immunisation with ZP3-antigens in accordance with the present invention.

Example 2

Expression of ZP3 in Human Prostate Cancer Cell Line (PC-)

Expression of the Zona Pellucida 3 protein (ZP3) in the human prostate cancer cell line (PC-) and prostate cancer was demonstrated at mRNA (A) and protein level (B) using standard RT-PR and western blot electrohoresis techniques. As expected single bands of RT-PR product (183 bp) and western blot electrophoresis (55 kDa) were observed (FIGS. 4A and B). Total mRNA and protein from normal human ovary (hOV) and testis (hTE) have been used as positive and negative control respectively.

Cytoplasmic localization of the ZP3 was demonstrated in the PC-3 cells (FIG. 5A) by immunofluorescence visualization using goat anti-rabbit IgG-Alexa Flour 594 (red).

Screening of the total mRNAs from prostate cancer samples scored as a Gleason 6-9 (n=10) by RT-PCR affirmed presence of the DNA products (183 bp) equivalent to the fragment of ZP3 (FIG. 6). Moreover, prostate samples were checked for the presence of the androgen receptor (AR) and luteinizing hormone-releasing hormone receptor (LHR) expression which remain important in the development (AR) and progression (AR and LHR) of prostate cancer (Heinlein and Chang7; Pinski et al.8).

DESCRIPTION OF THE FIGURES

FIG. 5: Immunofluorescence visualization of cytoplasmic localization of the ZP3 in PC-3 cells.

REFERENCES

Figure 1A:
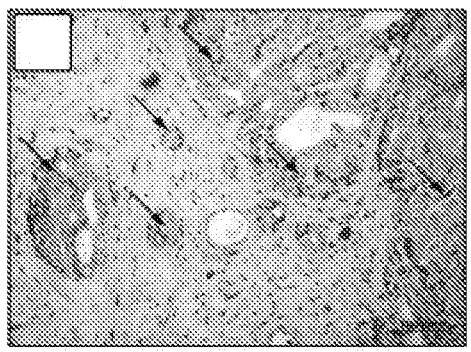
FIG. 1: histology (HE) of the human prostate adenocarcinoma (A, B), normal prostate (C) and normal human testis (D). Cancer glands are marked by arrows.
Figure 1B:
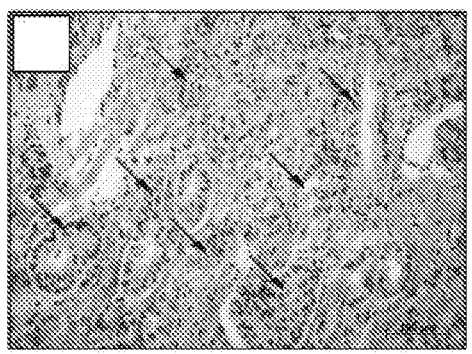
Figure 1C:
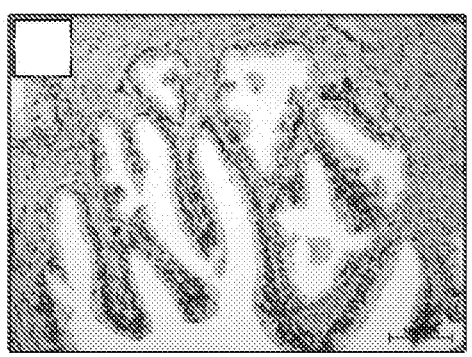
Figure 1D:
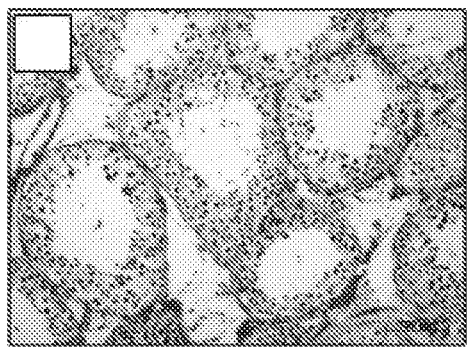
Figure 2A:
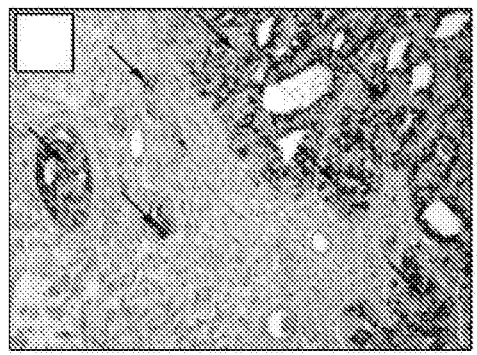
FIG. 2: the dubel α-methylacyl coenzyme A racemase (AMACR (red)) and cytokeratin 5/6 (CK5/6 (brown)) immunohistochemical staining in the human prostate adenocarcinoma (A, B), normal prostate (C) and in the normal human testis (D). The double immune-staining was performed as additional markers to the histology for the proper evaluation of the prostate specimens (Trpkov et al.9). Secretory carcinoma epithelial cells of the prostate glands showed strong circumferential cytoplasmic finely granular red staining for AMACR (A, B, arrows) and were negative for CK5/6 (positive for the basal epithelial cells of the normal prostate). Typical CK5/6 dark brown staining of the basal cells was observed in the normal prostatic epithelium which is negative for AMACR (L). Sections of human testis used as a negative control for the double immune-staining stayed negative for both AMACR, and CK5/6 (D).
Figure 2B:
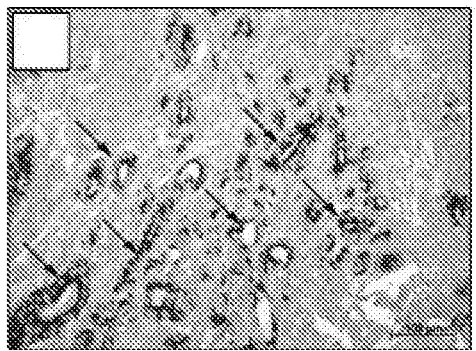
Figure 2C:
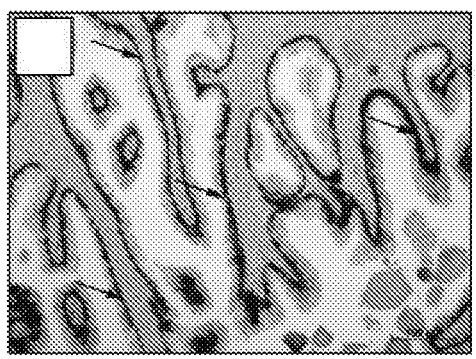
Figure 2D:
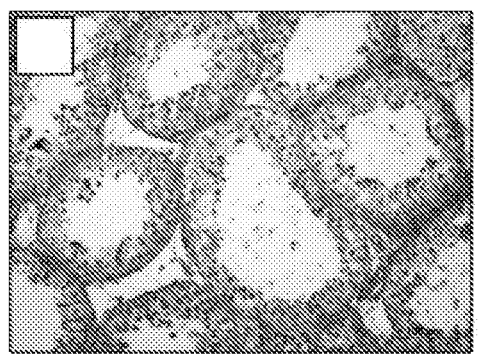
Figure 3A:
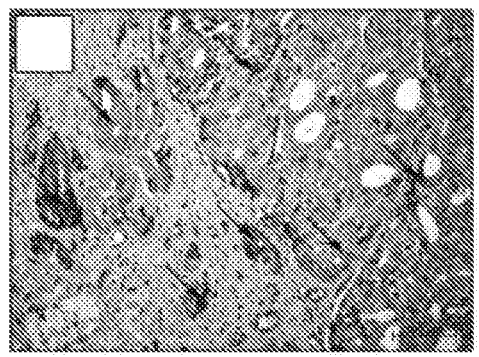
FIG. 3: single ZP3 immunohistochemical staining (brown) in the human prostate adenocarcinoma (A, B), normal prostate (C) and in the normal human testis (D). Positive and specific cytoplasmic staining for ZP3 was observed in cancer gland/tissue of the prostatic carcinoma stained positively for AMACR and negatively for CK5/6 (A, B). Normal human prostate was free of staining for ZP3 similarly to AMACR but not CK5/6 (C). Sections of the human testis were negative for ZP3 (D).
Figure 3B:
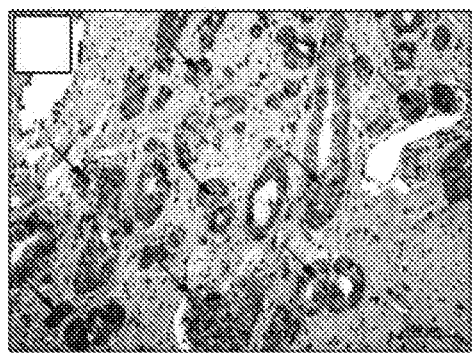
Figure 3C:
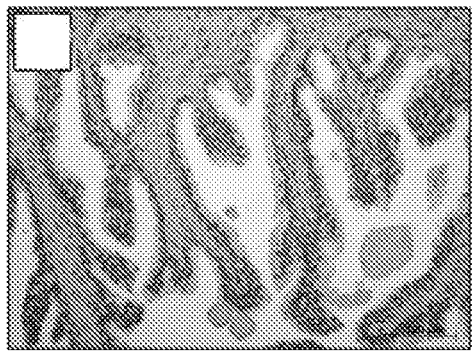
Figure 3D:
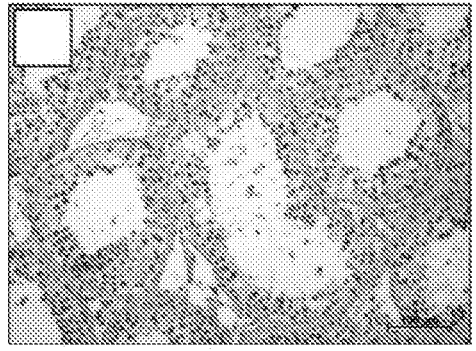
Figure 4A:
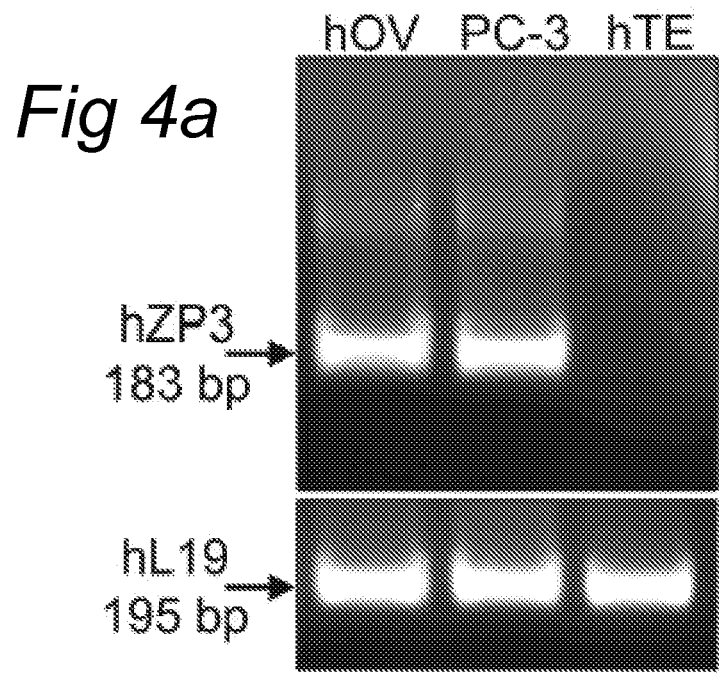
FIG. 4: Expression of the Zona Pellucida 3 protein (ZP3) in the human prostate cancer cell line (PC-) and prostate cancer at mRNA (A) and protein level (B).
Figure 4B:
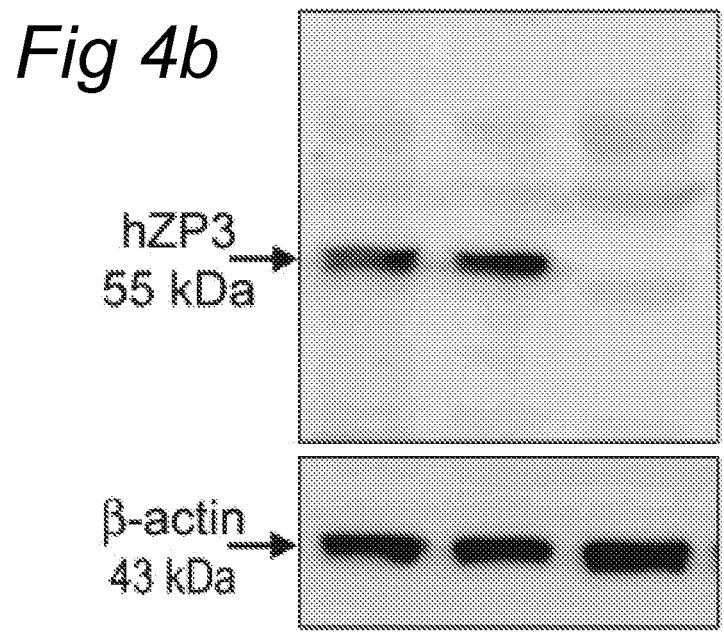
Figure 6:
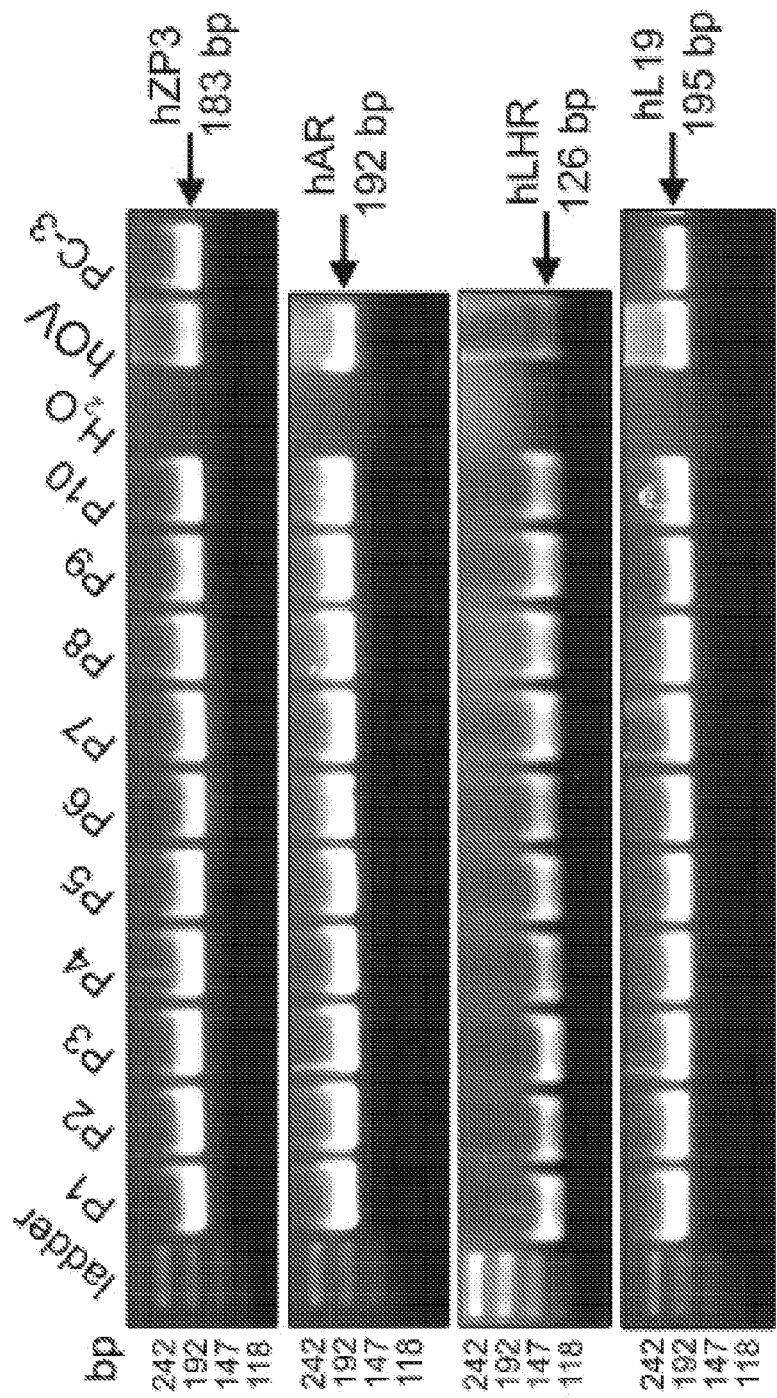
FIG. 6: total mRNAs from prostate cancer samples scored as a Gleason 6-9 (n=10) by RT-PCR to determine presence ZP3, androgen receptor (AR) and luteinizing hormone-releasing hormone receptor (LHR).

1. Parker, K. C., M. A. Bednarek, and J. E. Coligan. 1994. Scheme for ranking potential HLA-A2 binding peptides based on independent binding of individual peptide sidechains. J. Immunol. 152:163. HLA_BIND (http://bimas-.cit.nih.gov/molbio/hla_bind/)

2. Rammensee, Friede, Stevanovic, MHC ligands and peptide motifs: 1st listing, Immunogenetics 41, 178-228, 1995; SYFPEITHI (http://www.syfpeithi.de/) and Rammensee, Bachmann, Stevanovic: MHC ligands and peptide motifs. Landes Bioscience 1997 (International distributor—except North America: Springer Verlag GmbH & Co. KG, Tiergartenstr. 17, D-69121 Heidelberg 3. Buus S, Lauemoller S L, Worning P, Kesmir C, Frimurer T, Corbet S, Fomsgaard A, Hilden J, Holm A, Brunak S. Sensitive quantitative predictions of peptide-MHC binding by a 'Query by Committee' artificial neural network approach, in Tissue Antigens., 62:378-84, 2003; NetMHC (http://www.cbs.dtu.dk/services/NetMHC/)

4. Nielsen M, Lundegaard C, Worning P, Lauemoller S L, Lamberth K, Buus S, Brunak S, Lund O., Reliable prediction of T-cell epitopes using neural networks with novel sequence representations. Protein Sci., 12:1007-17, 2003.

5. Improved prediction of MHC class I and class II epitopes using a novel Gibbs sampling approach, Nielsen M, Lundegaard C, Worning P, Hvid C S, Lamberth K, Buus S, Brunak S, Lund O., Bioinformatics, 20(9):1388-97, 2004.

6. Sturniolo, T. et al., Nature Biotechnology 17, 555-562, 1999, Generation of tissue-specific and promiscuous HLA ligand databases using DNA chips and virtual HLA class II matrices; TEPITOPE (http://www.vaccinome.com/pages/597444/).

7. Heinlein C A, Chang C. Androgen receptor in prostate cancer. Endocr Rev. 2004, 25(2):276-308.

8. Pinski J, Xiong S, Wang Q, Stanczyk F, Hawes D, Liu S V. Effect of luteinizing hormone on the steroidogenic pathway in prostate cancer. Prostate. 2011, 71(8):892-8.

9. Trpkov K, Bartczak-McKay J, Yilmaz A. Usefulness of cytokeratin 5/6 and AMACR applied as double sequential immunostains for diagnostic assessment of problematic prostate specimens. Am J Clin Pathol. 2009; 132(2):211-20.

The invention claimed is:

1. A method for therapy or for reducing recurrence of prostate cancer and/or for therapy or reducing occurrence of prostate cancer metastases in a male human subject in need thereof, comprising administering to the subject an effective amount of:
 (a) a purified human zona pellucida 3 (hZP3) glycoprotein, the amino acid backbone of which has the amino acid sequence SEQ ID NO:3;
 (b) purified hZP3 polypeptide, the sequence of which is SEQ ID NO:3;
 (c) a purified glycoprotein or polypeptide that is an allelic variant of (a) or (b);
 (d) an immunologically active fragment of the hZP3 glycoprotein of (a), or of the polypeptide of (b) or the allelic variant of (c), that comprises:
  (i) a class I MHC-restricted hZP3 T cell epitope, and/or
  (ii) a class II MHC-restricted hZP3 T cell epitope,
  which fragment induces an immune response to native hZP3 glycoprotein in a human male,
 or
 (e) an expression vector comprising a nucleic acid molecule that encodes (b), (c) or (d).

2. The method according to claim 1, comprising administering to the subject the purified hZP3 glycoprotein of (a), the purified hZP3 polypeptide of (b); or the immunologically active fragment of (d).

3. The method according to claim 1 wherein the allelic variant results from a single nucleotide polymorphism in the nucleotide sequence encoding SEQ ID NO:3.

4. The method according to claim 1, comprising administering to the subject said immunologically active fragment of (d).

5. The method according to claim 1 wherein the length of said fragment is between 18 and 45 amino acid residues.

6. The method according to claim 1, wherein the immunologically active fragment comprises at least:
 (a) 50%; or
 (b) 70%; or
 (c) 90%; or
 (d) 95%
of the of the complete amino acid sequence of the amino acid backbone of said hZP3 glycoprotein (SEQ ID NO:3) or of said hZP3 polypeptide (SEQ ID NO:3).

7. The method according to claim 6 wherein said immunologically active fragment comprises at least 90% of the complete amino acid backbone of said hZP3 glycoprotein (SEQ ID NO:3) or said hZP3 polypeptide (SEQ ID NO:3).

8. The method according to claim 2, comprising administering to the subject the purified hZP3 polypeptide.

9. The method according to claim 1, wherein the hZP3 polypeptide of (b), the allelic variant of (c) or the fragment of (d) is glycosylated.

10. The method according to claim 9, wherein the glycosylated hZP3 polypeptide, allelic variant polypeptide, or fragment has the glycosylation pattern of native hZP3 glycoprotein or allelic variant glycoprotein or a corresponding glycopeptide fragment thereof.

11. The method according to claim 1 that further comprises administering or co-administering an adjuvant to the subject.

12. The method according to claim 1 wherein said administering results in therapy of said prostate cancer and/or metastases.

13. The method according to claim 1 wherein said administering results in reducing the occurrence of said metastases and/or recurrence of prostate cancer in the subject.

14. The method according to claim 1 that further comprises surgery, radiotherapy, High Intensity Focused Ultrasound treatment, hormonal therapy, chemotherapy, or a combination thereof.

15. The method according to claim 14 wherein said surgery is cryosurgery.

16. The method according to claim 14 wherein said radiotherapy is brachytherapy plus external beam radiation.

17. The method according to claim 1 wherein the hZP3 glycoprotein of (a), the hZP3 polypeptide of (b), the allelic variant glycoprotein or polypeptide of (c), the immunologically active fragment of (d), or the expression vector of (e) is administered as a pharmaceutical composition that also comprises a pharmaceutically acceptable carrier.

18. The method according to claim 17 wherein said administering results in therapy of said prostate cancer and/or metastases.

19. The method according to claim 17 wherein said administering results in reducing (i) the occurrence of said metastases and/or (ii) the recurrence of prostate cancer in the subject.

20. The method according to claim 1, comprising administering to the subject the vector comprising the nucleic acid molecule that encodes the hZP3 polypeptide of (b).

21. The method according to claim 1, comprising administering to the subject the vector comprising the nucleic acid molecule that encodes the allelic variant polypeptide of (c).

22. The method according to claim 1, comprising administering to the subject the vector comprising the nucleic acid molecule that encodes the immunologically active fragment of (d).

* * * * *

SEQUENCE LISTING

<160> NUMBER OF SEQ ID NOS: 4

<210> SEQ ID NO 1
<211> LENGTH: 638
<212> TYPE: PRT
<213> ORGANISM: human

<400> SEQUENCE: 1

```
Met Ala Gly Gly Ser Ala Thr Thr Trp Gly Tyr Pro Val Ala Leu Leu
1               5                   10                  15

Leu Leu Val Ala Thr Leu Gly Leu Gly Arg Trp Leu Gln Pro Asp Pro
            20                  25                  30

Gly Leu Pro Gly Leu Arg His Ser Tyr Asp Cys Gly Ile Lys Gly Met
        35                  40                  45

Gln Leu Leu Val Phe Pro Arg Pro Gly Gln Thr Leu Arg Phe Lys Val
    50                  55                  60

Val Asp Glu Phe Gly Asn Arg Phe Asp Val Asn Asn Cys Ser Ile Cys
65                  70                  75                  80

Tyr His Trp Val Thr Ser Arg Pro Gln Glu Pro Ala Val Phe Ser Ala
                85                  90                  95

Asp Tyr Arg Gly Cys His Val Leu Glu Lys Asp Gly Arg Phe His Leu
            100                 105                 110

Arg Val Phe Met Glu Ala Val Leu Pro Asn Gly Arg Val Asp Val Ala
        115                 120                 125

Gln Asp Ala Thr Leu Ile Cys Pro Lys Pro Asp Pro Ser Arg Thr Leu
    130                 135                 140

Asp Ser Gln Leu Ala Pro Pro Ala Met Phe Ser Val Ser Thr Pro Gln
145                 150                 155                 160

Thr Leu Ser Phe Leu Pro Thr Ser Gly His Thr Ser Gln Gly Ser Gly
                165                 170                 175

His Ala Phe Pro Ser Pro Leu Asp Pro Gly His Ser Ser Val His Pro
            180                 185                 190

Thr Pro Ala Leu Pro Ser Pro Gly Pro Gly Pro Thr Leu Ala Thr Leu
        195                 200                 205

Ala Gln Pro His Trp Gly Thr Leu Glu His Trp Asp Val Asn Lys Arg
    210                 215                 220

Asp Tyr Ile Gly Thr His Leu Ser Gln Glu Gln Cys Gln Val Ala Ser
225                 230                 235                 240

Gly His Leu Pro Cys Ile Val Arg Arg Thr Ser Lys Glu Ala Cys Gln
                245                 250                 255

Gln Ala Gly Cys Cys Tyr Asp Asn Thr Arg Glu Val Pro Cys Tyr Tyr
            260                 265                 270

Gly Asn Thr Ala Thr Val Gln Cys Phe Arg Asp Gly Tyr Phe Val Leu
        275                 280                 285

Val Val Ser Gln Glu Met Ala Leu Thr His Arg Ile Thr Leu Ala Asn
    290                 295                 300

Ile His Leu Ala Tyr Ala Pro Thr Ser Cys Ser Pro Thr Gln His Thr
305                 310                 315                 320

Glu Ala Phe Val Val Phe Tyr Phe Pro Leu Thr His Cys Gly Thr Thr
                325                 330                 335

Met Gln Val Ala Gly Asp Gln Leu Ile Tyr Glu Asn Trp Leu Val Ser
            340                 345                 350

Gly Ile His Ile Gln Lys Gly Pro Gln Gly Ser Ile Thr Arg Asp Ser
        355                 360                 365
```

```
Thr Phe Gln Leu His Val Arg Cys Val Phe Asn Ala Ser Asp Phe Leu
    370                 375                 380
Pro Ile Gln Ala Ser Ile Phe Pro Pro Ser Pro Ala Pro Met Thr
385                 390                 395                 400
Gln Pro Gly Pro Leu Arg Leu Glu Leu Arg Ile Ala Lys Asp Glu Thr
                405                 410                 415
Phe Ser Ser Tyr Tyr Gly Glu Asp Tyr Pro Ile Val Arg Leu Leu
            420                 425                 430
Arg Glu Pro Val His Val Glu Arg Leu Leu Gln Arg Thr Asp Pro
        435                 440                 445
Asn Leu Val Leu Leu His Gln Cys Trp Gly Ala Pro Ser Ala Asn
    450                 455                 460
Pro Phe Gln Gln Pro Gln Trp Pro Ile Leu Ser Asp Gly Cys Pro Phe
465                 470                 475                 480
Lys Gly Asp Ser Tyr Arg Thr Gln Met Val Ala Leu Asp Gly Ala Thr
                485                 490                 495
Pro Phe Gln Ser His Tyr Gln Arg Phe Thr Val Ala Thr Phe Ala Leu
            500                 505                 510
Leu Asp Ser Gly Ser Gln Arg Ala Leu Arg Gly Leu Val Tyr Leu Phe
        515                 520                 525
Cys Ser Thr Ser Ala Cys His Thr Ser Gly Leu Glu Thr Cys Ser Thr
    530                 535                 540
Ala Cys Ser Thr Gly Thr Thr Arg Gln Arg Ser Ser Gly His Arg
545                 550                 555                 560
Asn Asp Thr Ala Arg Pro Gln Asp Ile Val Ser Ser Pro Gly Pro Val
                565                 570                 575
Gly Phe Glu Asp Ser Tyr Gly Gln Glu Pro Thr Leu Gly Pro Thr Asp
            580                 585                 590
Ser Asn Gly Asn Ser Ser Leu Arg Pro Leu Leu Trp Ala Val Leu Leu
        595                 600                 605
Leu Pro Ala Val Ala Leu Val Leu Gly Phe Gly Val Phe Val Gly Leu
    610                 615                 620
Ser Gln Thr Trp Ala Gln Lys Leu Trp Glu Ser Asn Arg Gln
625                 630                 635

<210> SEQ ID NO 2
<211> LENGTH: 745
<212> TYPE: PRT
<213> ORGANISM: human

<400> SEQUENCE: 2

Met Ala Cys Arg Gln Arg Gly Gly Ser Trp Ser Pro Ser Gly Trp Phe
1               5                   10                  15
Asn Ala Gly Trp Ser Thr Tyr Arg Ser Ile Ser Leu Phe Phe Ala Leu
            20                  25                  30
Val Thr Ser Gly Asn Ser Ile Asp Val Ser Gln Leu Val Asn Pro Ala
        35                  40                  45
Phe Pro Gly Thr Val Thr Cys Asp Glu Arg Glu Ile Thr Val Glu Phe
    50                  55                  60
Pro Ser Ser Pro Gly Thr Lys Lys Trp His Ala Ser Val Asp Pro
65                  70                  75                  80
Leu Gly Leu Asp Met Pro Asn Cys Thr Tyr Ile Leu Asp Pro Glu Lys
                85                  90                  95
Leu Thr Leu Arg Ala Thr Tyr Asp Asn Cys Thr Arg Arg Val His Gly
            100                 105                 110
```

```
Gly His Gln Met Thr Ile Arg Val Met Asn Asn Ser Ala Ala Leu Arg
        115                 120                 125

His Gly Ala Val Met Tyr Gln Phe Phe Cys Pro Ala Met Gln Val Glu
        130                 135                 140

Glu Thr Gln Gly Leu Ser Ala Ser Thr Ile Cys Gln Lys Asp Phe Met
145                 150                 155                 160

Ser Phe Ser Leu Pro Arg Val Phe Ser Gly Leu Ala Asp Asp Ser Lys
                165                 170                 175

Gly Thr Lys Val Gln Met Gly Trp Ser Ile Glu Val Gly Asp Gly Ala
                180                 185                 190

Arg Ala Lys Thr Leu Thr Leu Pro Glu Ala Met Lys Glu Gly Phe Ser
                195                 200                 205

Leu Leu Ile Asp Asn His Arg Met Thr Phe His Val Pro Phe Asn Ala
        210                 215                 220

Thr Gly Val Thr His Tyr Val Gln Gly Asn Ser His Leu Tyr Met Val
225                 230                 235                 240

Ser Leu Lys Leu Thr Phe Ile Ser Pro Gly Gln Lys Val Ile Phe Ser
                245                 250                 255

Ser Gln Ala Ile Cys Ala Pro Asp Pro Val Thr Cys Asn Ala Thr His
                260                 265                 270

Met Thr Leu Thr Ile Pro Glu Phe Pro Gly Lys Leu Lys Ser Val Ser
        275                 280                 285

Phe Glu Asn Gln Asn Ile Asp Val Ser Gln Leu His Asp Asn Gly Ile
        290                 295                 300

Asp Leu Glu Ala Thr Asn Gly Met Lys Leu His Phe Ser Lys Thr Leu
305                 310                 315                 320

Leu Lys Thr Lys Leu Ser Glu Lys Cys Leu Leu His Gln Phe Tyr Leu
                325                 330                 335

Ala Ser Leu Lys Leu Thr Phe Leu Leu Arg Pro Glu Thr Val Ser Met
                340                 345                 350

Val Ile Tyr Pro Glu Cys Leu Cys Glu Ser Pro Val Ser Ile Val Thr
        355                 360                 365

Gly Glu Leu Cys Thr Gln Asp Gly Phe Met Asp Val Glu Val Tyr Ser
        370                 375                 380

Tyr Gln Thr Gln Pro Ala Leu Asp Leu Gly Thr Leu Arg Val Gly Asn
385                 390                 395                 400

Ser Ser Cys Gln Pro Val Phe Glu Ala Gln Ser Gln Gly Leu Val Arg
                405                 410                 415

Phe His Ile Pro Leu Asn Gly Cys Gly Thr Arg Tyr Lys Phe Glu Asp
                420                 425                 430

Asp Lys Val Val Tyr Glu Asn Glu Ile His Ala Leu Trp Thr Asp Phe
                435                 440                 445

Pro Pro Ser Lys Ile Ser Arg Asp Ser Glu Phe Arg Met Thr Val Lys
        450                 455                 460

Cys Ser Tyr Ser Arg Asn Asp Met Leu Leu Asn Ile Asn Val Glu Ser
465                 470                 475                 480

Leu Thr Pro Pro Val Ala Ser Val Lys Leu Gly Pro Phe Thr Leu Ile
                485                 490                 495

Leu Gln Ser Tyr Pro Asp Asn Ser Tyr Gln Gln Pro Tyr Gly Glu Asn
                500                 505                 510

Glu Tyr Pro Leu Val Arg Phe Leu Arg Gln Pro Ile Tyr Met Glu Val
        515                 520                 525
```

```
Arg Val Leu Asn Arg Asp Asp Pro Asn Ile Lys Leu Val Leu Asp Asp
            530                 535                 540

Cys Trp Ala Thr Ser Thr Met Asp Pro Asp Ser Phe Pro Gln Trp Asn
545                 550                 555                 560

Val Val Val Asp Gly Cys Ala Tyr Asp Leu Asp Asn Tyr Gln Thr Thr
                565                 570                 575

Phe His Pro Val Gly Ser Ser Val Thr His Pro Asp His Tyr Gln Arg
            580                 585                 590

Phe Asp Met Lys Ala Phe Ala Phe Val Ser Glu Ala His Val Leu Ser
            595                 600                 605

Ser Leu Val Tyr Phe His Cys Ser Ala Leu Ile Cys Asn Arg Leu Ser
            610                 615                 620

Pro Asp Ser Pro Leu Cys Ser Val Thr Cys Pro Val Ser Ser Arg His
625                 630                 635                 640

Arg Arg Ala Thr Gly Ala Thr Glu Ala Glu Lys Met Thr Val Ser Leu
                645                 650                 655

Pro Gly Pro Ile Leu Leu Leu Ser Asp Asp Ser Ser Phe Arg Gly Val
            660                 665                 670

Gly Ser Ser Asp Leu Lys Ala Ser Gly Ser Ser Gly Glu Lys Ser Arg
            675                 680                 685

Ser Glu Thr Gly Glu Glu Val Gly Ser Arg Gly Ala Met Asp Thr Lys
            690                 695                 700

Gly His Lys Thr Ala Gly Asp Val Gly Ser Lys Ala Val Ala Ala Val
705                 710                 715                 720

Ala Ala Phe Ala Gly Val Val Ala Thr Leu Gly Phe Ile Tyr Tyr Leu
                725                 730                 735

Tyr Glu Lys Arg Thr Val Ser Asn His
            740                 745

<210> SEQ ID NO 3
<211> LENGTH: 424
<212> TYPE: PRT
<213> ORGANISM: human

<400> SEQUENCE: 3

Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
            115                 120                 125

Val Arg Thr Asn Arg Ala Glu Ile Pro Ile Glu Cys Arg Tyr Pro Arg
        130                 135                 140

Gln Gly Asn Val Ser Ser Gln Ala Ile Leu Pro Thr Trp Leu Pro Phe
145                 150                 155                 160
```

Arg Thr Thr Val Phe Ser Glu Glu Lys Leu Thr Phe Ser Leu Arg Leu
                165                 170                 175

Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
        275                 280                 285

Ala Glu Gln Asp Pro Asp Glu Leu Asn Lys Ala Cys Ser Phe Ser Lys
    290                 295                 300

Pro Ser Asn Ser Trp Phe Pro Val Glu Gly Pro Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
            340                 345                 350

His Val Thr Glu Glu Ala Asp Val Thr Val Gly Pro Leu Ile Phe Leu
        355                 360                 365

Asp Arg Arg Gly Asp His Glu Val Gln Trp Ala Leu Pro Ser Asp
    370                 375                 380

Thr Ser Val Val Leu Leu Gly Val Gly Leu Ala Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
            420

<210> SEQ ID NO 4
<211> LENGTH: 540
<212> TYPE: PRT
<213> ORGANISM: human

<400> SEQUENCE: 4

Met Trp Leu Leu Arg Cys Val Leu Leu Cys Val Ser Leu Ser Leu Ala
1               5                   10                  15

Val Ser Gly Gln His Lys Pro Glu Ala Pro Asp Tyr Ser Ser Val Leu
            20                  25                  30

His Cys Gly Pro Trp Ser Phe Gln Phe Ala Val Asn Leu Asn Gln Glu
        35                  40                  45

Ala Thr Ser Pro Pro Val Leu Ile Ala Trp Asp Asn Gln Gly Leu Leu
    50                  55                  60

His Glu Leu Gln Asn Asp Ser Asp Cys Gly Thr Trp Ile Arg Lys Gly
65                  70                  75                  80

Pro Gly Ser Ser Val Val Leu Glu Ala Thr Tyr Ser Ser Cys Tyr Val
                85                  90                  95

```
Thr Glu Trp Asp Ser His Tyr Ile Met Pro Val Gly Val Glu Gly Ala
            100                 105                 110

Gly Ala Ala Glu His Lys Val Val Thr Glu Arg Lys Leu Leu Lys Cys
        115                 120                 125

Pro Met Asp Leu Leu Ala Arg Asp Ala Pro Asp Thr Asp Trp Cys Asp
    130                 135                 140

Ser Ile Pro Ala Arg Asp Arg Leu Pro Cys Ala Pro Ser Pro Ile Ser
145                 150                 155                 160

Arg Gly Asp Cys Glu Gly Leu Gly Cys Cys Tyr Ser Ser Glu Glu Val
                165                 170                 175

Asn Ser Cys Tyr Tyr Gly Asn Thr Val Thr Leu His Cys Thr Arg Glu
            180                 185                 190

Gly His Phe Ser Ile Ala Val Ser Arg Asn Val Thr Ser Pro Pro Leu
        195                 200                 205

Leu Leu Asp Ser Val Arg Leu Ala Leu Arg Asn Asp Ser Ala Cys Asn
    210                 215                 220

Pro Val Met Ala Thr Gln Ala Phe Val Leu Phe Gln Phe Pro Phe Thr
225                 230                 235                 240

Ser Cys Gly Thr Thr Arg Gln Ile Thr Gly Asp Arg Ala Val Tyr Glu
                245                 250                 255

Asn Glu Leu Val Ala Thr Arg Asp Val Lys Asn Gly Ser Arg Gly Ser
            260                 265                 270

Val Thr Arg Asp Ser Ile Phe Arg Leu His Val Ser Cys Ser Tyr Ser
        275                 280                 285

Val Ser Ser Asn Ser Leu Pro Ile Asn Val Gln Val Phe Thr Leu Pro
    290                 295                 300

Pro Pro Phe Pro Glu Thr Gln Pro Gly Pro Leu Thr Leu Glu Leu Gln
305                 310                 315                 320

Ile Ala Lys Asp Lys Asn Tyr Gly Ser Tyr Tyr Gly Val Gly Asp Tyr
                325                 330                 335

Pro Val Val Lys Leu Leu Arg Asp Pro Ile Tyr Val Glu Val Ser Ile
            340                 345                 350

Leu His Arg Thr Asp Pro Tyr Leu Gly Leu Leu Leu Gln Gln Cys Trp
        355                 360                 365

Ala Thr Pro Ser Thr Asp Pro Leu Ser Gln Pro Gln Trp Pro Ile Leu
    370                 375                 380

Val Lys Gly Cys Pro Tyr Ile Gly Asp Asn Tyr Gln Thr Gln Leu Ile
385                 390                 395                 400

Pro Val Gln Lys Ala Leu Asp Leu Pro Phe Pro Ser His His Gln Arg
                405                 410                 415

Phe Ser Ile Phe Thr Phe Ser Phe Val Asn Pro Thr Val Glu Lys Gln
            420                 425                 430

Ala Leu Arg Gly Pro Val His Leu His Cys Ser Val Ser Val Cys Gln
        435                 440                 445

Pro Ala Glu Thr Pro Ser Cys Val Val Thr Cys Pro Asp Leu Ser Arg
    450                 455                 460

Arg Arg Asn Phe Asp Asn Ser Ser Gln Asn Thr Thr Ala Ser Val Ser
465                 470                 475                 480

Ser Lys Gly Pro Met Ile Leu Leu Gln Ala Thr Lys Asp Pro Pro Glu
                485                 490                 495

Lys Leu Arg Val Pro Val Asp Ser Lys Val Leu Trp Val Ala Gly Leu
            500                 505                 510
```

```
Ser Gly Thr Leu Ile Leu Gly Ala Leu Leu Val Ser Tyr Leu Ala Val
        515                 520                 525

Lys Lys Gln Lys Ser Cys Pro Asp Gln Met Cys Gln
    530                 535                 540
```